United States Patent [19]
Belonenko et al.

[11] Patent Number: 5,804,698
[45] Date of Patent: Sep. 8, 1998

[54] METHOD AND SYSTEM FOR MEASURING FLUID PARAMETERS BY ULTRASONIC METHODS

[75] Inventors: Vladimir Belonenko, Moscow, Russian Federation; Tigran Chalikian, Piscatsway, N.J.; Leo Demaeyer; Theodor Funck, both of Göttingen, Germany; Armen Sarvazyan, Pushchino, Russian Federation

[73] Assignee: UHP Corp., Portola Valley, Calif.

[21] Appl. No.: 635,968

[22] PCT Filed: Oct. 28, 1994

[86] PCT No.: PCT/EP94/03548

§ 371 Date: Nov. 13, 1996

§ 102(e) Date: Nov. 13, 1996

[87] PCT Pub. No.: WO95/12123

PCT Pub. Date: May 4, 1995

[30] Foreign Application Priority Data

Oct. 29, 1993 [EP] European Pat. Off. ............. 93117619

[51] Int. Cl.[6] .................................................. G01H 5/00
[52] U.S. Cl. .............................. 73/1.83; 73/1.86; 73/645; 73/579; 73/32 A
[58] Field of Search ................................... 73/32 A, 645, 73/579, 1.83, 1.86; 340/621

[56] References Cited

U.S. PATENT DOCUMENTS 3,828,607  8/1974  Janzen et al. .

FOREIGN PATENT DOCUMENTS

| | | |
|---|---|---|
| 0430859A1 | 6/1991 | European Pat. Off. . |
| 0502197A1 | 9/1992 | European Pat. Off. . |
| A684437 | 8/1979 | U.S.S.R. . |
| 2236591 | 4/1991 | United Kingdom . |
| WO 9203723 | 3/1992 | WIPO . |
| WO 9308466 | 4/1993 | WIPO . |

OTHER PUBLICATIONS

A.P. Sarvazyan et al., *Theoretical Analysis of an Ultrasonic Interferometer for Precise Measurements at High Pressures*, Ultrasonics 1991, vol. 29, Mar. 30, 1990, pp. 119–124.

*Primary Examiner*—Christine K. Oda
*Attorney, Agent, or Firm*—Baker & Botts, L.L.P.

[57] ABSTRACT

A system for measuring fluid parameters of one or more liquids by an ultrasonic method comprises a voltage controlled oscillator; an ultrasonic resonator comprising one or more resonator cells, each of the resonator cells comprising an electro-acoustical transmitting transducer, an electro-acoustical receiving transducer, and a sample cavity between the transducers, wherein the transmitting transducer is connected to the output terminal of the voltage controlled oscillator; and a phase locked loop circuit comprising one of the resonator cells. The system also includes circuits for generating an ultrasonic frequency signal of variable frequency; applying the ultrasonic frequency signal to the transmitting transducer; responding to an output signal of the receiving transducer; providing a phase control voltage for controlling and varying the phase of the ultrasonic frequency signal; and providing a frequency control voltage for selecting a frequency of the ultrasonic frequency signal applied to the transmitting transducer according to a particular resonance peak of the resonator cells.

19 Claims, 9 Drawing Sheets

METHOD AND SYSTEM FOR MEASURING FLUID PARAMETERS BY ULTRASONIC METHODS

BACKGROUND OF THE INVENTION

1. Field of the Invention:

This invention relates to methods and systems for measuring fluid parameters by ultrasonic methods. More particularly, the system of the present invention uses ultrasonic methods for measuring thermodynamic properties of a liquid sample.

2. Description of the Related Art:

The function of the volume of a liquid vs. pressure and/or temperature ("P-V-T data") is of importance in many fields of science and technology. P-V-T data are the basis for a complete thermodynamic characterization of condensed matter, including liquids, by the respective equation of state.

Various methods for measuring P-V-T data are known in the art. Particularly promising are ultrasonic methods because of the inherent potential to obtain higher accuracies than most other methods, because the velocity of sound in condensed matter can be determined with an accuracy in the order of $10^6$.

Ultrasonic methods for determining parameters of a material generally involve the measuring of the velocity and optionally the attenuation of ultrasonic waves in the material to be investigated at various pressures and temperatures. The adiabatic compressibility of a material is directly correlated to the velocity of sound, thus, the P-V-T data of the material can be derived from measurements of the velocity of sound waves, particularly ultrasonic waves, at various pressures and temperatures, if the absolute value of the density of the material under investigation at the temperature of interest at normal pressure is known.

The acoustic impedance Z of a liquid is a function of its density $\rho$ and the velocity of sound c in the liquid:

$$Z=\rho c. \tag{1}$$

The acoustic resonances $f_n$ of a layer of a sample liquid in an acoustic resonator cell (in short "liquid resonances") and the resonances of the emitter and receiver transducers of the cell (which are assumed as equal) at the fundamental frequencies $f_0$, and at the odd multiples thereof are coupling with each other, causing a mutual interaction of these resonances. Therefore the reflection of sound waves in an ultrasonic resonator at the interfaces between the transducers and the sample liquid is a function of the acoustic impedance Z of the sample liquid and the acoustic impedance $Z_0$ of the transducer material.

The coupling effects are dependent on the differences of the frequency of the transducer resonance and the frequency of the respective resonance of the-liquid on the one hand, and on the acoustic impedances of the sample liquid and transducer material on the other hand.

More specific theoretical considerations of the behaviour of an ultrasonic resonator have shown that when the transducers are air-backed the reflection conditions at liquid resonance frequencies $f_n \approx nf_\pi (f_\pi = f_0/2)$ are almost ideal, i.e. the amplitudes and phases of the liquid resonances can be taken as independent of the resonances of the transducers. It is therefore easy to evaluate the values of the velocity and absorption of sound in the sample liquid at these frequencies.

However, liquid resonances near the resonance frequency of the transducers are adversely affected by the non-ideal conditions of sound wave reflection. This has been discussed in various theoretical treatises. In all these theoretical discussions the effects of the non-ideal reflection conditions on the liquid resonances are described as a function of the acoustic impedances of liquid and transducer material on the one hand, and as a function of the distance of the resonance frequency of the respective liquid resonance from the resonance frequency of the transducer on the other hand, see e.g. A. P. Sarvazyan and T. V. Chalikian, Ultrasonics 29 (1991) 119–124. If the acoustic impedance of the transducer material is known, the impedance of the sample liquid and hence its density can be evaluated from the changes of the liquid resonances caused by the non-ideal reflection conditions.

Sarvazyan and Chalikian (l. c.) also disclose an apparatus for ultrasonic measurements of liquid parameters. The apparatus includes an ultrasonic resonator cell which comprises a pair of electro-acoustical transducers defining at least one resonator cavity containing a liquid to be investigated. The resonator cell is positioned in a pressure vessel containing a pressurizing fluid which pressurizes the sample and backs the transducers.

It is known from SU-A-68437 to determine the density of a liquid from resonance frequencies of liquid resonances by means of semi-empirical equations. The application of these equations requires the measurement of resonance frequencies of the liquid under investigation in the vicinity of the transducer resonance, where the quality of the resonances is decreased considerably, i. e. the resonance peaks are unduly broadened. Thus, the measurements of the resonance frequencies can be carried out with limited accuracy only and the accuracy of the density values obtained by this method is unsufficient for precise results of P-V-T evaluations. However, an exact determination of the density of a liquid under examination is an indispensable requisite of reliable P-V-T measurements.

SUMMARY OF THE INVENTION

It is therefore an object of the invention to provide novel methods and apparatus for accurately measuring parameters of condensed matter, especially liquids, by an ultrasonic resonator method.

A further object of the invention is to provide methods and apparatus for automatically measuring P-V-T parameters of liquids, including the absolute value of the density of the liquid, by an ultrasonic resonator method.

A new and more accurate measurement procedure for the densities of liquid samples using the quality factors of liquid resonances has been invented. The quality factors of the liquid resonances are derived from the half-power bandwidths (HPBW) $\Delta f_n$, which are determined by the amplitude vs frequency or phase vs frequency characteristics of liquid resonance peaks. Even if only broad resonances are available, where the frequency at the maximum amplitude is not well defined, the amplitude level $A_{max}$ at the resonance maximum can be determined with high precision by averaging to eliminate the noise near the maximum. The frequencies f' and f" at the amplitude values corresponding to 0.707 $A_{max}$ (or any other suitable value) on either sides of the resonance maximum can be measured with sufficient accuracy because the resonance curve is rather steep at these amplitude levels. As a consequence the accuracy of the $\Delta f_n$ value is independent from the accuracy of a direct measurement of the resonance frequency $f_n$. A still more accurate determination of the resonance frequency is achieved by arithmetically averaging the half-power frequencies, if the resonance peak is symmetrical above the level 0.707 $A_{max}$.

The quality factor of a liquid are derived from the half-power bandwidths (HPBW) $\Delta f_n$ or other suitable power levels, which are determined from the amplitude vs. frquency characteristics of liquid resonance peaks. In an equivalent manner the phase vs. frequency characteristics of the resonances may be used for evaluation of the center frequency and quality factor. The position of the steepest part of the phase vs. frequency characteristic corresponds to the center of resonance, the slope of the phase characteristic is a direct function of the quality factor.

DESCRIPTION OF THE PREFERRED EMBODIMENTS

Figure 1:
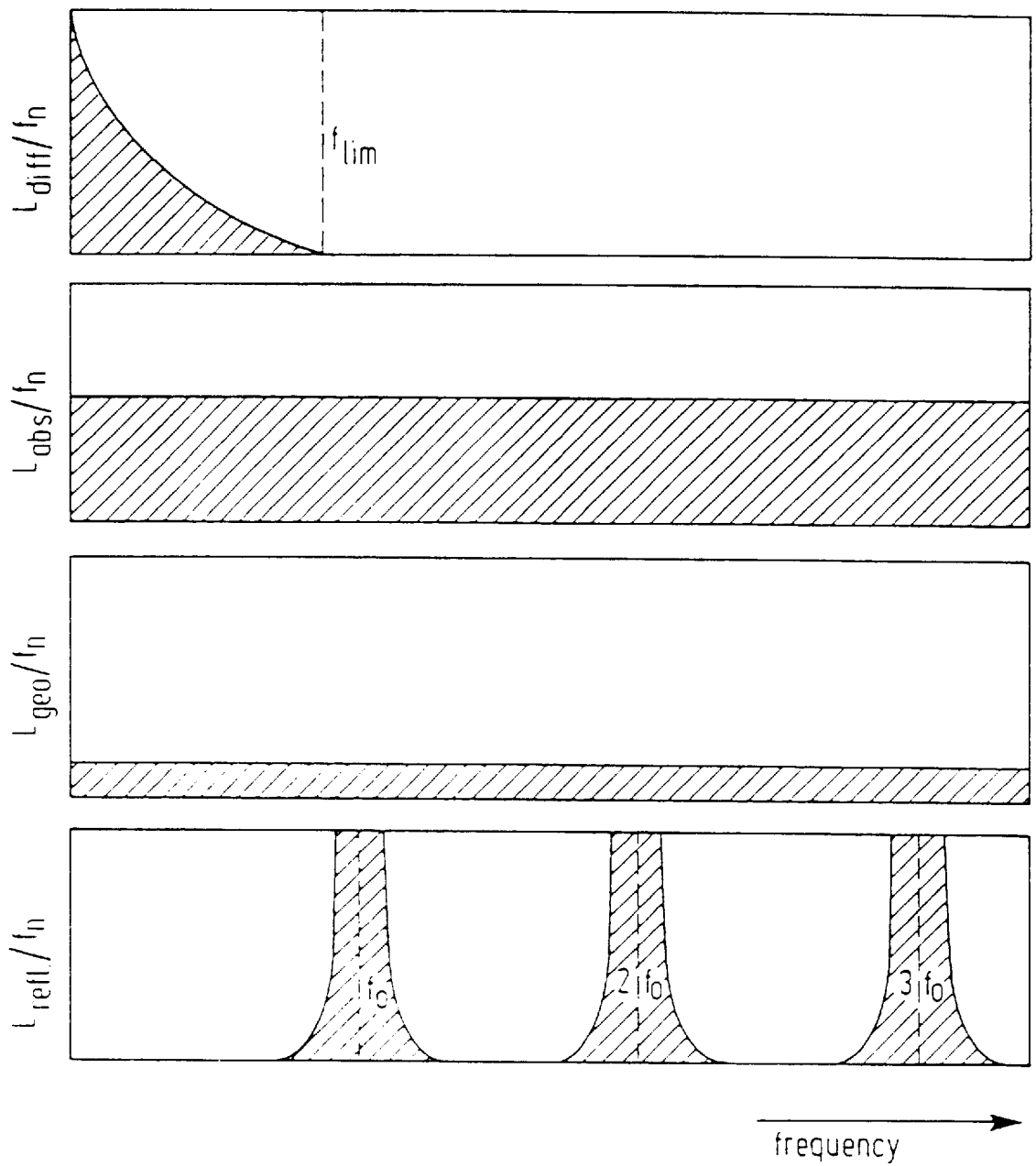
FIG. 1 is a diagram of the components of the losses occuring in an ultrasonic resonator cell vs. fequency.

In the following, the term "ultrasonic liquid resonator" is used for an ultrasonic resonator comprising a pair of flat circular disc-shaped electro-acoustical transducers of the same diameter mounted parallel to each other in a fixed distance to define a cavity for receiving a sample liquid.

Characteristic parameters of ultrasonic liquid resonators are $r_0$=effective radius of the transducers;

d=distance of the transducers (=pathlength of the ultrasound waves in the cavity);

$f_0$=fundamental resonance frequency of transducers (assumed as equal for both transducers);

$f_n$=frequency of amplitude maximum of liquid resonance #n, $\Delta f_n$=HPBW of liquid resonance at frequency $f_n$;

$Q_n$=quality factor Q of resonance at frequency $f_n$: $Q_n=f_n/\Delta f_n$;

$\lambda$=wavelength of ultrasound wave in the cavity.

The loss occuring in an ultrasonic liquid resonator at the resonance frequency $f_n$ can be defined as:

$$L_n = 1/Q_n = \Delta f_n/f_n \quad (2)$$

and is the sum of the four following loss components, which are additive and can be described quantitatively:

(i) Loss $L_{abs}$ caused by the absorption by the sample liquid. For liquids exhibiting no relaxation in the frequency range under investigation this contribution is a linear function of $f_n$.

(ii) Loss $L_{diff}$ caused by diffraction in the range of low frequencies, where the absorption of sound is low and therefore the travelling distance of the sound waves in the resonator is relatively long. In addition, in the range of low frequencies the radiation from the transducers is strongly affected by the characteristics of the sound field, which is dependent on the ratio of $r_0$ and $\lambda$. This loss component decreases rapidly with increasing frequency according to a more complex function of $f_n$. An important feature of this function is that $L_{diff}$ is decreasing practically to zero at a limiting frequency $f_{lim}$ which is characteristic for each individual resonator and can be calculated from $r_0$, c and the sound absorption coefficient∝ of the sample liquid sample:

$$f_{lim} = \sqrt[3]{\frac{c}{r_0^2(\alpha/f^2)}} \quad (3)$$

(iii) A further loss component ($L_{geo}$) which is also a linear function of $f_n$, is caused by the limitation of the sound beam by the configuration of the ultrasonic resonator cavity.

(iv) Finally a fourth loss component $L_{refl}$ observed near the resonance frequencies of the transducers is caused by the non-ideal reflection conditions at the surfaces-of the. transducers. As a first oder approach for $L_{refl}$ the following equation may be used:

$$L_{refl} = \frac{f_{refl}}{f_n} = \frac{-c \ln(\cos\theta)}{\pi d f_n} \quad (4)$$

see e. g. A. P. Saravazyan et al, Ultrasonics 29 (1991) 119–124.

DETERMINATION OF DENSITY OF LIQUIDS BY ULTRASONIC RESONATOR MEASUREMENTS

All measurements are carried out using a P-V-T resonator cell filled with a sample of the liquid which is to be investigated by P-V-T techniques. The cell is operated in air rather than being immersed in a pressurized liquid. The quantitative treatment of resonators with air-backed transducers leads to simpler equations and therefore a more precise determination of the density is possible under these conditions.

First $f_{lim}$ of the used resonator cell filled with the sample liquid is calculated. The accuracies of ∝ and c for the calculation of $f_{lim}$ are not critical, because they are contributing to the value of $f_{lim}$ only by their cubic roots. Therefore even approximate values of ∝ and of c can be used. The precision of $r_0$ is more important, but as whole this calculation is not very critical because it yields only a lower frequency limit, and all measurements should be carried out well above this limit.

The next step is the measurement of $L_{abs}+L_{geo}$ at a frequency $f_n$ which is close to an odd multiple of ($f_\pi=f_0/2$) but well above $f_{lim}$. Since $$(L_{abs}+L_{geo})/f_n = \Delta f_{abs+geo}/f_n^2 = \epsilon_{abs+geo} = \text{constant} \quad (5)$$

for all frequencies of the resonator these loss components can be calculated at each resonance frequency.

In the third step liquid resonances under non-ideal reflection conditions near odd multiples of $f_0$ are measured and from the results the density of the sample liquid is evaluated.

For this purpose the $\Delta f_n$ values of one or more liquid resonances on both sides of the resonance frequency of the transducer are measured. Usefull for later averaging is the measurement at pairs of resonances $f_{n1}$ and $f_{n2}$, where the resonance should have approximately the same distance from the center of the transducer resonance frequency, $n_{fo}-f_{n1}\approx f_{n2}-n_{fo}$. From these $\Delta f_n$ values the corresponding values of $L_{refl}$ and $\Delta f_{refl}$ are derived:

$$\Delta f_{refl} = \Delta f_n - \epsilon_{abs+geo}f_n^2 \quad (6)$$

Then $-\ln(\cos\theta)$ is calculated using Equation (4).

Several methods may be used for the evaluation of $\theta$ from $-\ln(\cos\theta)$. It is important to not e that the use of approximations in this step by which the accuracy of the $\Delta f_n$ measurements may be affected will directly decrease the accuracy of the final density value.

Figure 2:
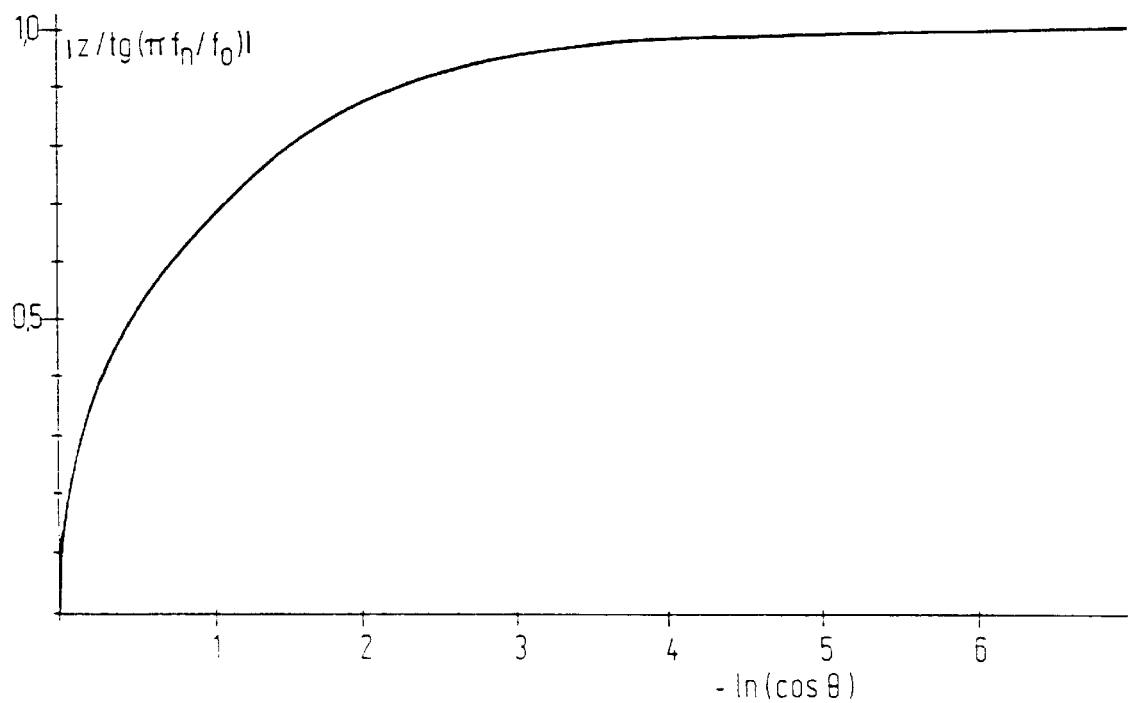
FIG. 2 is a diagram of a function useful in the present method.

It is preferred to evaluate the value of $J=z/tg(\pi f_n/f_0)$ directly from the $-\ln(\cos\theta)$ value. This is possible by approximation by an appropriate function (see FIG. 2) or more preferably by the use of a look-up table (see Appendix) which contains precise numerical data of the corresponding magnitudes. The relation between both magnitudes is a smooth function (see FIG. 2) so that linear interpolation of discrete values is easily possible. In an automatic evaluation an electronic look-up table may be used. Such an operation can be easily carried out with considerable precision as practical values of z occur only in a narrow numerical range. The acoustic impedances of practically all liquids (with the exclusion of mercury) at 20° C. are between $0.708\times10^6$ [kg/m$^2$s] for hexane, $1.50\times10^6$ [kg/m$^2$s] for water $2.42\times10^6$ [kg/m$^2$s] for glycerol, $2.68\times10^6$ [kg/m$^2$s] for bromoform.

The range in which the first order approximation of Eq. (4) and Eq. (5) is applicable depends on the acoustic impedances of of the tranducers and of the sample liquid, leading to the following limits of applicability for transducers made of quartz ($Z_0=15.105\times10^6$[kg/m$^2$s]) and of lithium niobate ($Z_0=34.404\times10^6$[kg/m$^2$s]):

| Transducer/Substance | z | Frequency limit f' for $f_n$ near $f_0$ |
| --- | --- | --- |
| Quartz/Glycerol | 0.1602 | $f^* = f_{2\pi}1 \pm 0.051$) |
| Lithium niobate/Hexane | 0.0206 | $f^* = f_{2\pi}(1 \pm 0.007)$ |
| Quartz/Water | 0.0993 | $f^* = f_{2\pi}(1 \pm 0.032)$ |
| Lithium niobate/Water | 0.0436 | $f^* = f_{2\pi}(1 \pm 0.014)$ |

The frequency limits f' given above are theoretical limits. Actually the precision of evaluation is reduced in a wider frequency range on both sides of the transducer resonance.

Using Eqs. (7) and (8) the ratio of acoustic impedances z and the density can easily be calculated:

$$z = J\, tg(\pi f_n/f_0) \tag{7}$$

$$\rho = \frac{Z_0 z}{c} \tag{8}$$

In order to increase the precision and reliability of the evaluation procedure the effective transducer resonance frequency should be calculated from corresponding pairs of liquid resonances on both sides of the transducer resonance. Also the effective acoustic impedance of the transducers should be evaluated from resonances of the reference cell filled with water. Suitable averaging procedures can be carried out using data of several liquid resonances or data of corresponding pairs of resonances on both sides of the transducer resonance.

Figure 3:
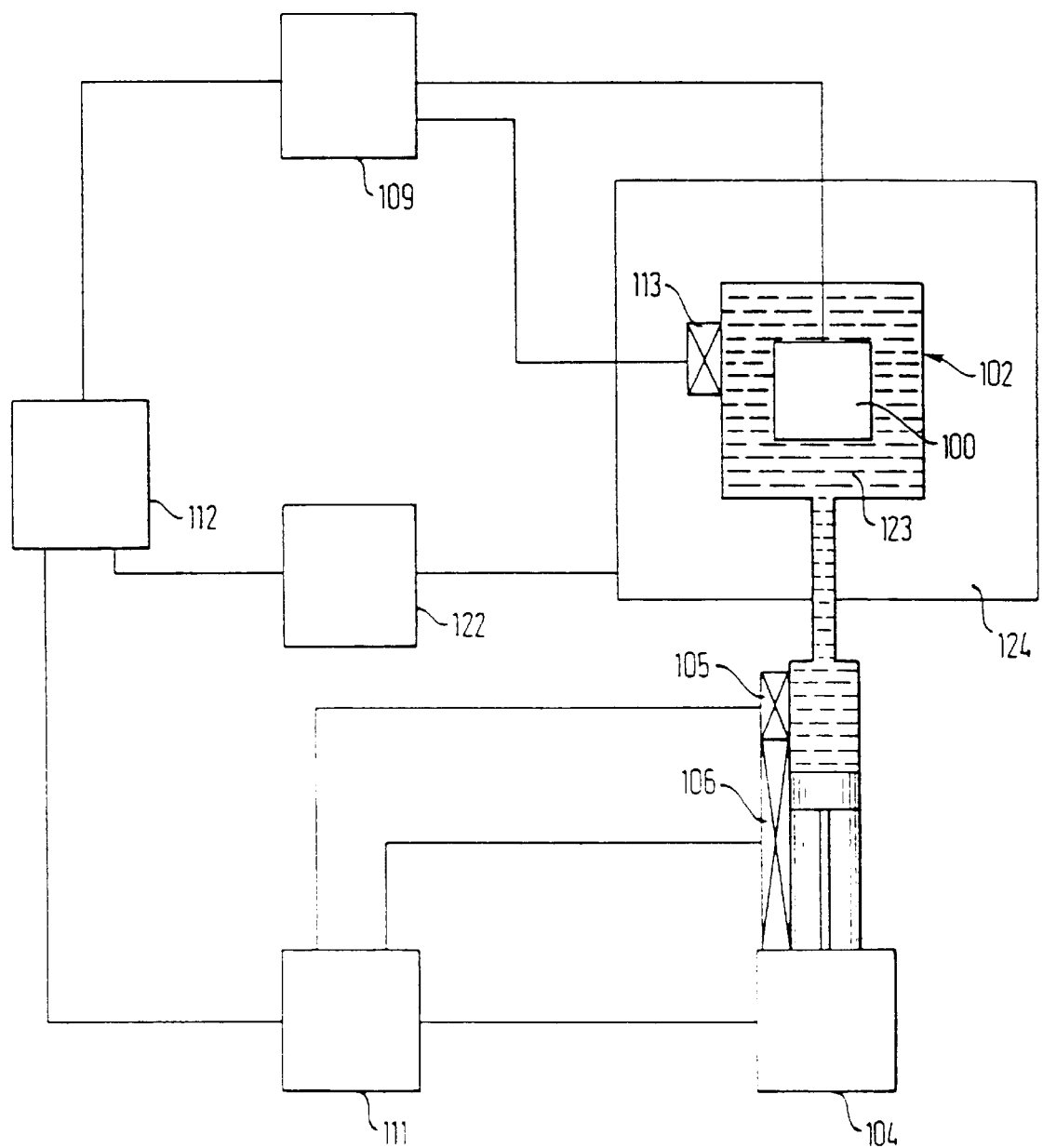
FIG. 3 is a diagram of various steps of an embodiment of the method according to the invention.

FIG. 3 shows, partly in section partly in block diagram form, essential components of an ultrasonic measuring system for measuring P-V-T data of a liquid sample. It comprises acoustical resonator cells 100 positioned in a pressure vessel 102 which is filled with a pressure transmitting liquid 123. The pressure transmitting liquid is pressurized by a high pressure piston pump 104 which includes actuating means, such as an electric motor unit controlled by an electronic control unit 111. An appropriate pump is being described in Applicant's co-pending international patent application No. PCT/EP93/01840.

The displacement of the pump piston relative to a pump cylinder is sensed by a displacement sensor 106. The pressure within the pump cylinder is sensed by a force sensor 105. Output signals of the sensors 105, 106 are fed back to the control unit 111. Generally, the system further comprises an automatically operating circuitry 109 for sensing electrical characteristics of acousticals resonators which will be explained below. Some of these acoustical resonators are liquid resonator cells combined in cell 100. The temperature of the cell 100 is closely controlled by a thermostat 124 within which the pressure vessel is mounted. The thermostat is controlled by a control unit 122. For P-V-T measurements of high precision the expansion of the pressurized system must be taken into account. A stress sensor or acoustical transducer 113 is coupled to the pressure vessel. This system may operate as an acoustical resonator monitored by using the circuitry 109.

A memory and control unit 112 provides for control of the various units mentioned above.

Figure 4:
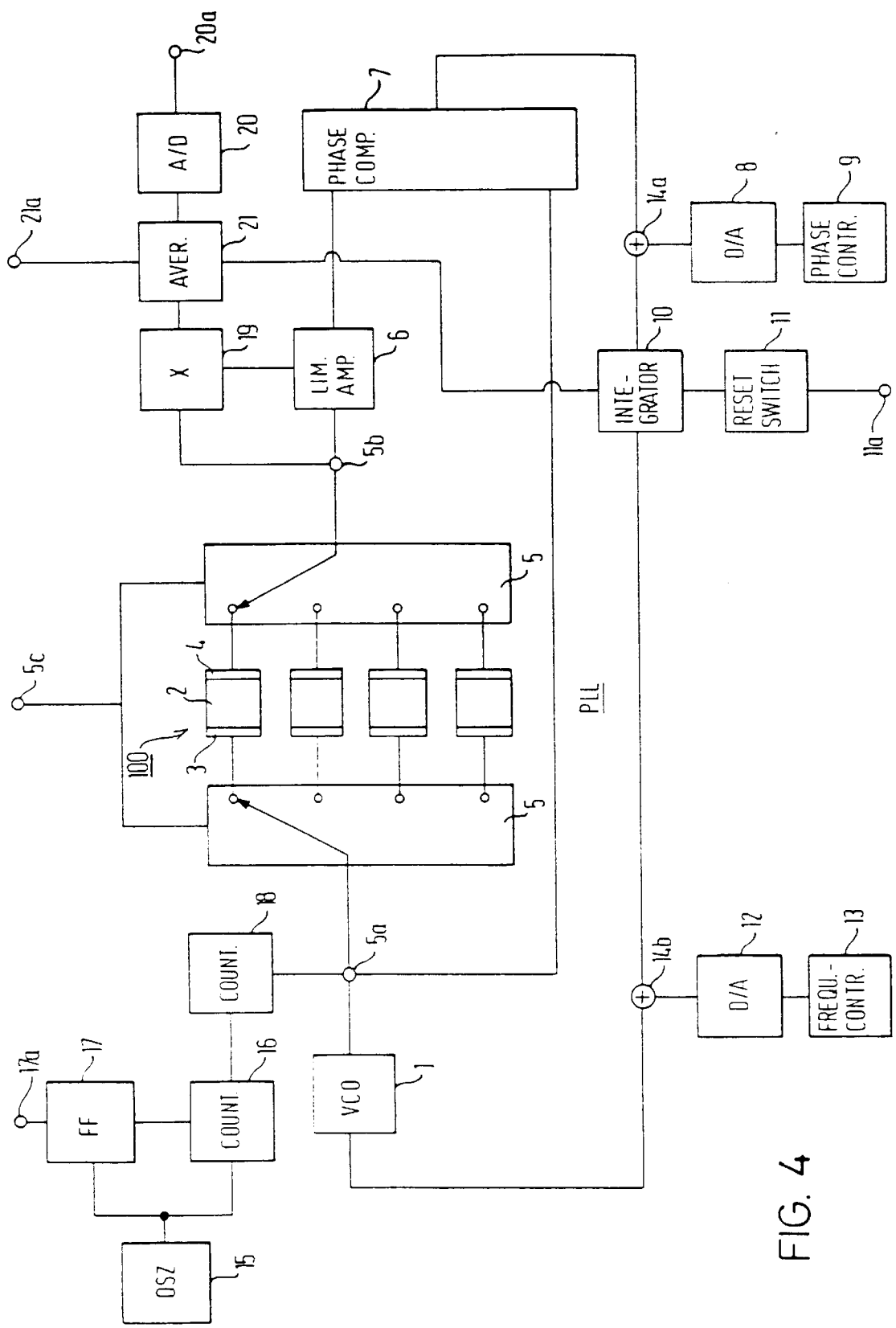
FIG. 4 is a diagrammatic view, partly in section, partly in block form, of an ultrasonic measuring system in which the invention may be embodied.

The system of FIG. 4 which comprises a preferred embodiment of the invention, includes a plurality of acoustical resonator cells 100 each including an electro-acoustical transmitter transducer 3, a cavity 2, and an electro-acoustical receiver transducer 4. The resonator cells are coupled as shown between selector switch means 5 which has a control terminal 5c and is adapted to connect, under control of a control signal applied to terminal 5c, any desired cell 100 between a switch input terminal 5a and a switch output terminal 5b. A voltage controlled oscillator VCO 1 has an output coupled to the input terminal 5a, and a control input. The frequency of VCO 1 is controlled via an electronic feedback path connected to the control input whereby an output signal provided by the receiving piezoelectric transducer 4 of the selected cell has a well defined phase difference with respect to the driving voltage supplied from oscillator 1 to the transmitting transducer 3 of this cell. The feedback loop is part of a phase-locked loop which locks the oscillator 1 to a frequency defined by a resonance frequency of the resonator cell and by the phase difference between the driving signal and the output signal of the selected acoustical cell 100. This phase difference can be selected externally as will be explained below. The oscillator output is further used as phase reference for a pulse generating circuit 7 operating as phase comparator. Means may be provided to invert the phase reference signal under external control.

The PLL including the feedback path comprises the following components:

a) The voltage controlled oscillator VCO 1 which is of a type which produces an output frequency which is a monotonous function of an input control voltage applied to said control input. The amplitude of the output voltage of VCO 1 should be independent of the frequency of operation of the VCO.

b) The two-part selector switch 5 comprising an input section and an output section which each operate as a single-pole multithrow switch, couples a desired cell 100 into the PLL.

c) A limiting amplifier circuit 6 which receives the signal from the ouput of the selected cell 100 and forms it into a square wave having the sign or polarity of the received signal and preserving its phase.

d) A phase comparator circuit 7 which constitutes a high impedance current source producing unidirectional pulses of constant amplitude and a duration which is proportional to the phase difference between the driving oscillator 1 ouput signal and the output signal of the amplifier circuit 6.

e) An adder circuit 14a having a first input coupled to receive the output signal of the phase comparator 7, and a second input coupled to the output of a digital-to-analog (D/A) converter circuit 8 for providing a first variable voltage which serves as phase control voltage. Circuit 8 receives a digital phase control signal from control circuit 9 which may comprise a PC or other suitable control means.

f) An integrating circuit 10 having its input connected to an output terminal of adder circuit 14a to provide an output voltage proportional to the time integral of the sum of the current pulses from phase comparator 7 representing the phase difference, and of an opposing current proportional to the adjustable phase control voltage. The integrating circuit 10 is controlled by an externally controllable switch 11, which has a control terminal 11a and which, when actuated, resets the integrator output voltage to a defined level e. g. ground potential. This will deactivate the feedback path from phase detector 7 to VCO 1 and, thus, interrupt the PLL.

h) A second adder circuit 14b having a first input connected to the output of the integrating circuit 10 and a second input coupled to a further digital-to-analog converter circuit 12 for providing a second variable voltage (frequency control voltage). Circuit 12 receives a digital frequeny control input signal from the PC or other suitable control means. An ouput terminal of the adder circuit 14b is coupled to the control input of VCO, thus, closing the loop.

The circuitry of FIG. 4 further comprises circuitry for measuring the frequency of the output signal of the oscillator and the amplitude of the cell output signal.

The circuitry for measuring the oscillator frequency comprises a timer circuit including a quartz oscillator 15 providing clock pulses, a presettable counter 16 providing a timer interval by counting the clock pulse down from a preset number to zero, and a flipflop circuit 17 for synchronizing an external start signal, applied to a terminal 17a, with the clock pulses so that the start and the termination of the timer interval established by the timer circuit coincides with the clock pulses. The timer circuit controls the counting period of a counter circuit 18 which receives the VCO 1 output signal.

The circuitry for generating a signal representing the amplitude of the cell 100 output signal comprises a multiplier circuit 19 in which the output signal at the output terminal 5b is multiplied by its own sign, i.e. by a corresponding signal of like polarity obtained from the limiting amplifier 6, and the resulting signal is averaged in an averaging circuit 21 having a control input terminal 21a for receiving a time constant control signal, and then processed by a unit 20 which comprises an analog-to-digital converter coupled to an output terminal 20a for connecting a digital display or the PC.

As mentioned above, switch 11 in combination with integrator 10 forms means for interrupting the feedback path by disconnecting integrator 10 from adder 14b under external control so that the system can operate as a conventional network analyzer in which the frequency of the oscillator is controlled solely by the output of the circuit 12. In this case the integrating circuit 10 operates as low-pass amplifier receiving a sole input from the phase detector 7 and supplying an output signal which represents the phase of the signal received from the resonator cell. Such signal may be selected as an alternate input rather than the output of circuit 19 to the A/D converter of unit 20 by using an externally controlled analog multiplexer 21. The multiplexer switches required for this mode of operation equally may be incorporated in the components 10, 8 and 20.

A first mode of operation of the circuit of FIG. 4 is the network analyser mode. In this mode the frequency of VCO 1 is stepped over a predetermined range of frequencies by stepwise variation of the input voltage of the frequency control D/A converter in unit 13. At each step the frequency is measured by counting the oscillator 1 oscillations by the counter 18 for a period of time determined by the timer circuit 15, 16, 17. This counting interval is selected by the control voltage applied to terminal 17a. The period of counting should be adequate to the desired accuracy and may be in practice between 10 and 100 milliseconds for a VCO frequency in the megahertz range. Further, the timing interval should be long enough to enable a plurality of measurements of the amplitude and the phase of the signal delivered at this frequency from the selected resonator cell 100. These measurements may be averaged for improving the accuracy. As a result, a phase-frequency and an amplitude-frequency diagram over a frequency range including several resonance frequencies of the cell is obtained. This information is used to determine the input voltage of the frequency control D/A converter in unit 13 for selecting a desired resonance in this range.

A second mode of operation which usually is initiated after the frequency control D/A converter unit has been set on a particular desired resonance, and the phase control D/A converter in unit 9 has been set to an appropriate value within the locking range of the phase comparator 7, is the PLL mode of operation which is turned on by closing the feedback path, i. e. by activating integrator 10 by an appropriate control signal level at terminal 11a. In this mode of operation, the input voltage of the phase control D/A converter is varied stepwise. For each step, the frequency of the oscillator 1 is determined. During each frequency counting interval multiple amplitude measurements and measurements of other parameters, e.g. temperature and pressure of the sample, are carried out and averaged.

The system can be switched to another resonance frequency of the selected cell by temporarily closing the externally controlled switch 11 for a short period of time (which interrupts the feedback path) and changing the setting of the frequency control voltage during this period. The duration of the interruption must be sufficiently long to allow VCO 1 to stabilize on the new frequency. A change of the frequency control voltage while switch 11 is open and, thus the integrator 10 being operative and coupled into the feedback path, does not change the operating frequency of the VCO since the feedback path will compensate any change of the voltage at the output of circuit 12 by a corresponding opposing change of the output voltage of the integrator 10.

Figure 5:
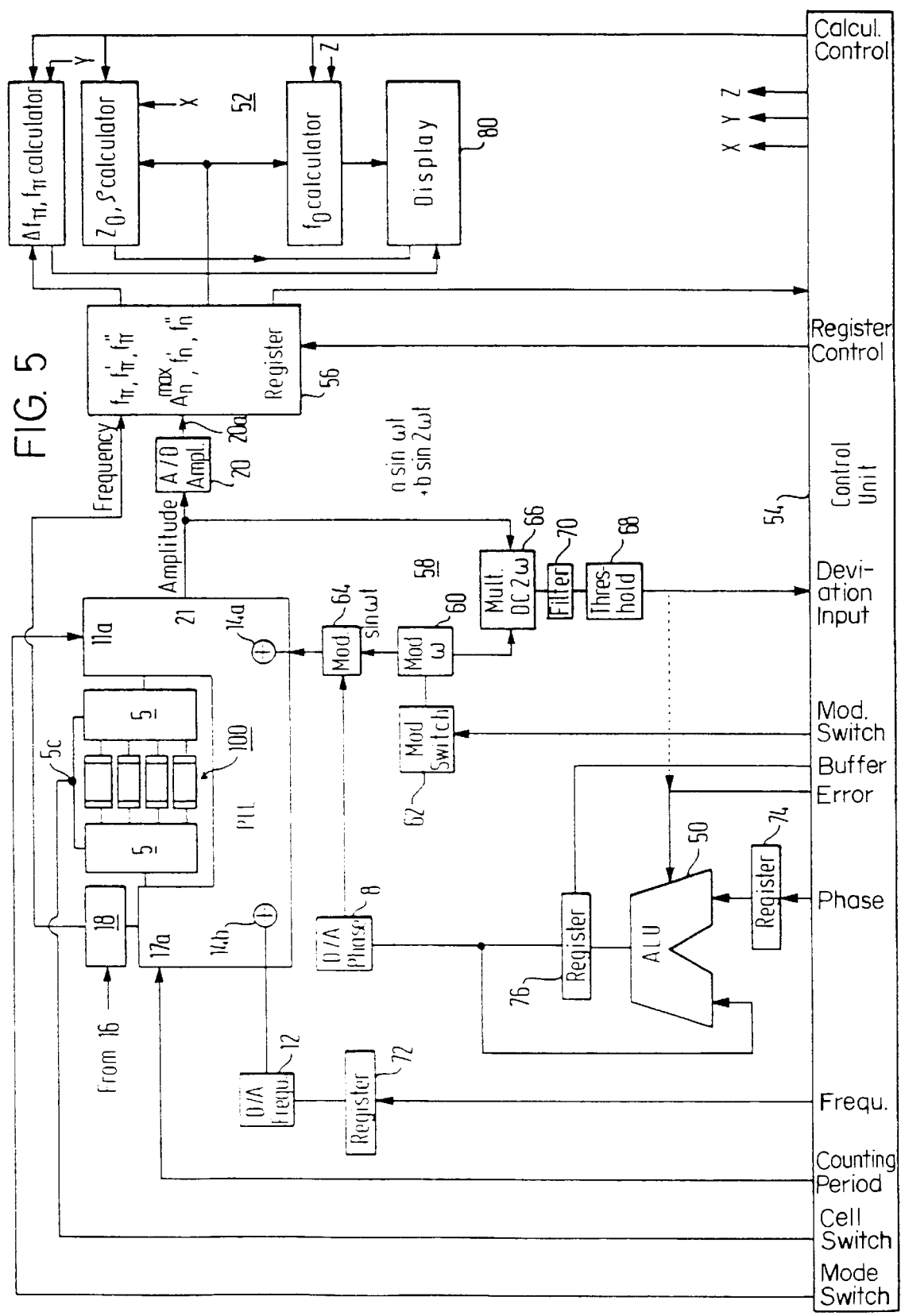
FIG. 5 is a diagram of an electronic circuit useful in a system of the type shown in FIG. 4.

The system of FIG. 5 is a preferred embodiment of the invention and comprises a circuitry of the type shown in and described with reference to FIG. 4. Thus, like reference numerals are used in FIGS. 4 and 5 for similar elements.

The system of FIG. 5 comprises a phase-locked loop PLL similar to that shown in and described with reference to FIG. 4. Further main components of the system of FIG. 5 are an arithmetic logic unit ALU 50, a calculation circuitry 52 and a control unit 54 which may comprise a microprocessor.

The system of FIG. 5 further includes a register 56 for storing frequency and amplitude values for processing by the calculation circuitry 52, and a modulating circuit 58 for modulating the analog phase control voltage provided by D/A 8 with a sine wave modulating signal. The modulating circuit includes a modulation voltage source 60 providing a sinusoidal modulating signal of a frequency which is low compared with the frequency of the ultrasonic waves; further a modulator switch 62 for activating or desactivating the modulating signal generator 60, and a modulator 64 which receives the phase control voltage from D/A 8 and the output signal of the generator 60 and delivers a modulated phase control signal to adder 14a.

The modulating signal is further coupled to a first input of a multiplier circuit 66 which has a second input receiving the amplitude representative signal from the output of averaging circuit 21.

An output terminal of the multiplier circuit 66 is coupled to an error or deviation signal generating circuit via a low pass filter 70. The circuit which provides a deviation signal to a deviation signal input of control unit 54. The deviation signal is zero when the filtered output signal of the multiplier 66 falls between predetermined positive and negative threshold values which are alike and close to zero, a positive (increment) signal when the output signal exceeds the positive threshold, and a negative (increment) signal when the output falls below the negative threshold. A first buffer register 72 is coupled between a frequency control output terminal of control unit 54 and the input terminal of D/A 12. A second buffer register 74 is coupled between a phase control signal terminal of the control unit and a corresponding input of ALU 50, and a third buffer register 76 is coupled between the output of ALU and the input of D/A 8. The output of register 76 is fed back to a further input of ALU.

When the density and other P-V-T parameters of a liquid is to be determined by means of the system of FIG. 5, one of the cells 100 is filled with a sample of the liquid and another cell is filled with a reference liquid, such as water. The remaining cells may be filled with other liquids to be investigated. It is assumed that the characteristics of all cells 100 of the system of FIG. 5 are essentially equal.

In advance, the frequency limit $f_{lim}$ of a cell 100 is determined as explained above and the frequency range within which the ultrasonic measurements are made, is set well above $f_{lim}$ in a freqency range register (not shown) in the controlled unit 54.

When a measuring cycle is started, the control unit 54 first selects the reference cell by applying an appropriate control signal to terminal 5c. The PLL is set in the network analyser mode by applying an appropriate signal to terminal 11a. By applying an appropriate frequency control signal to D/A 12, the frequency of the VCO 1 (FIG. 4) is swept over the full preset frequency range which is above $f_{lim}$. The frequency is changed by stepwise incrementation of the buffered digital input to the D/A 12. The resonances of the ultrasonic waves in the reference cell which occur during the sweep are detected as explained above and stored in register 56.

Then the system is switched in the PLL mode in which the feedback path of the PLL is closed, and the frequency is set to a selected first liquid resonance by an appropriate signal applied to D/A 12. In this mode, the maximum amplitude of the resonance peak is detected by a digital feedback mechanism: The phase control voltage at terminal 14a of the PLL is modulated by the sine wave signal from modulator 60 by a modulating frequency ω. The output signal of the resonator cell is then $$U_{out} = a \sin \omega t + b \sin 2\omega t.$$

Multiplication of $U_{out}$ with the modulating signal in multiplier 66 produces a signal consisting of a DC component and an AC component of frequency 2ω. After a filtering off the AC component, the DC component is analyzed by zero voltage detector 68. The detector 68 exits a digital output signal of the value zero when the absolute value of the DC component is lower than a preselected threshold near zero. For positive DC components exceeding the threshold, detector 68 produces a positive increment signal and for negative DC components exceeding the threshold, detector 68 produces a negative increment signal.

In this mode of operation, the ALU unit 50 which has buffered input and output, shifts the phase number by digital feedback to the phase number of the resonance maximum and keeps it at this value, enabling an accurate counting of the frequency and measuring of the amplitude at the resonance maximum.

The maximum amplitude, phase and the frequency of the maximum are stored in the register 56 of the calculating circuitry.

Then in the PLL mode of operation, frequencies f' and f" at preset amplitude levels or phase values on the right and left side of the resonance maximum are measured by variation of the phase values applied to the phase D/A 8 from ALU 50 via register 56. By this means, the characteristic data of the subsequent resonance peaks are obtained and transferred into register 56.

The switch 5 is then set to a selected sample cell and the above procedure is repeated for each sample cell.

Figure 6:
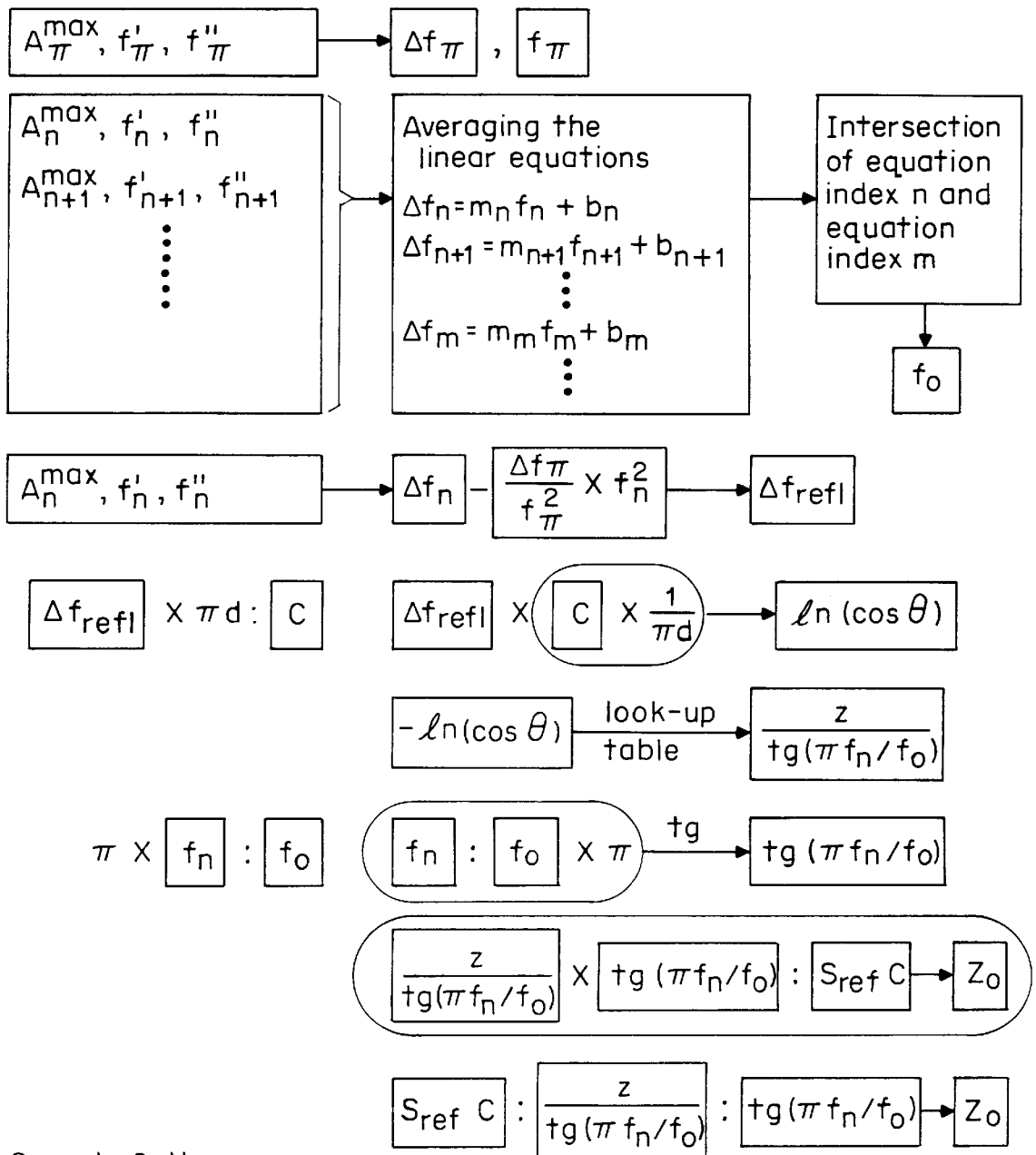
FIG. 6 is a diagram of various steps of an embodiment of the method according to the invention.

Under control of the control unit 54, the calculating unit 52 calculates the acoustical impedance Z and eventually the density o of the investigated liquid according to the scheme shown in FIG. 6 under control of the control unit. $\Delta f_\pi$ and $f_\pi$ are the HPBW and resonance frequency respectively, near odd multiples of $f_o/2$.

Figure 7:
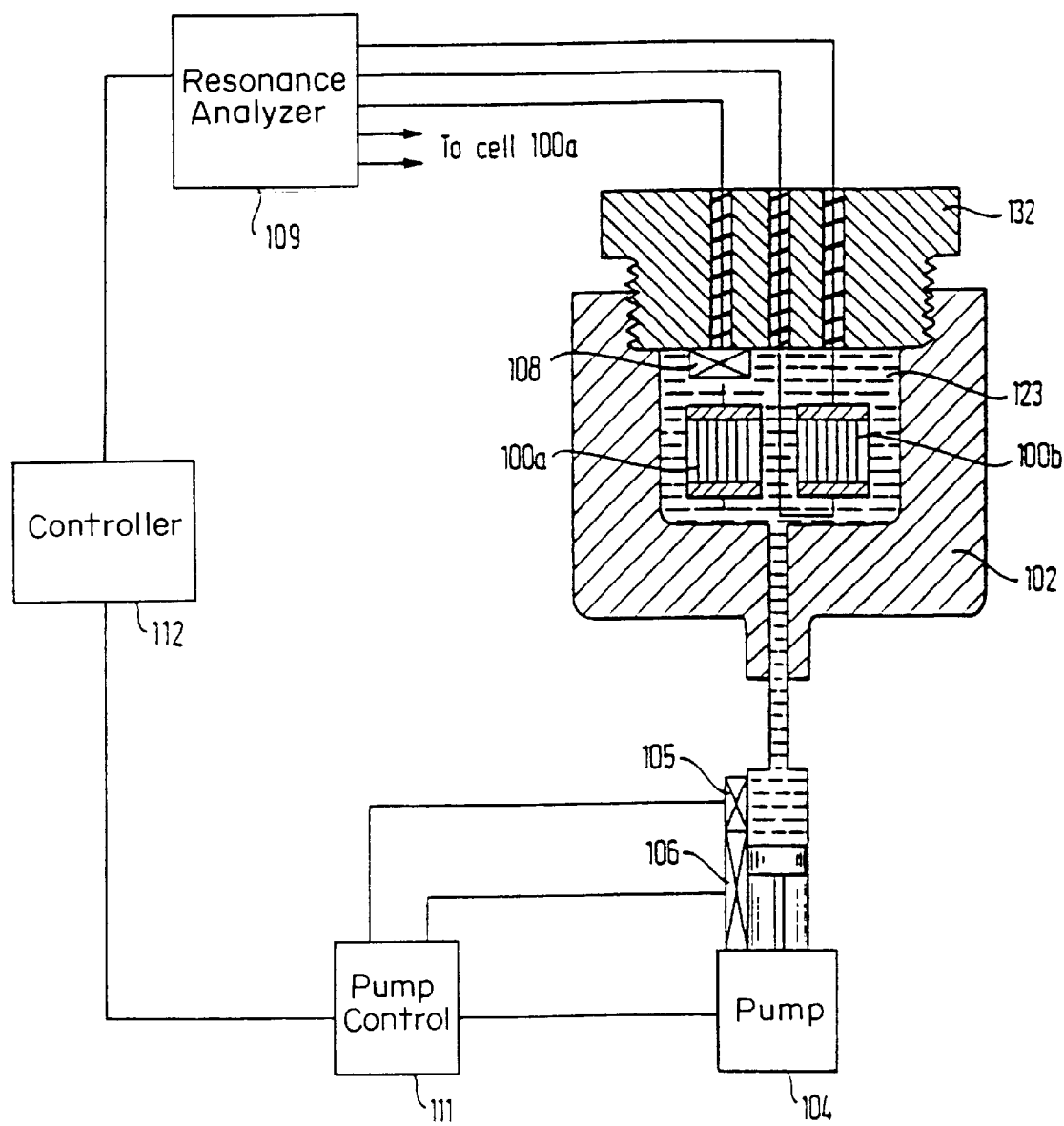
FIG. 7 to FIG. 9 show further ultrasonic measuring systems in which the invention can be embodied.

FIG. 7 shows a schematic illustration of a further embodiment of the invention. A vessel 102 being pressure-tightly closed by a cover 132, e.g. by a pressure tight-thread, contains the fluid 123 to be pressurized by means of pump 104. Also included in said vessel are at least two acoustical resonator cells 100a and 100b, one of which may be used as a reference cell for establishing a relative standard while using the other cell(s) is/are used as sample cell(s) for relative measurements against the standard. Also included in the inner chamber of vessel 102 is a solid-state pressure sensitive resonator 108 allowing fast determination of a reference condition within fluid 123. This resonator may be used to quickly adjust the system to a desired resonance condition with less accuracy whereby more precise measurements thereafter may be obtained by switching over to a resonator cell 100. Of course, it will be possible to arrange more than two resonator cells within vessel 102, if desired, when the chamber within the vessel will be large enough. If one cell will be used as a reference cell the other cells are available for measurements. Should all cells be needed for measurements and the required accuracy is not too high, resonator 108 may be used for resonance measurements.

The output signals of all units located within vessel 102 are conducted pressure-tightly through cover 132 to circuit 109 which transforms the received signals into a form appropriate for application to memory and control circuit 112. This circuit 112 provides the commands necessary for controlling pump control circuit 111 which in turn provides for extreme precise control of pump 104.

Figure 8:
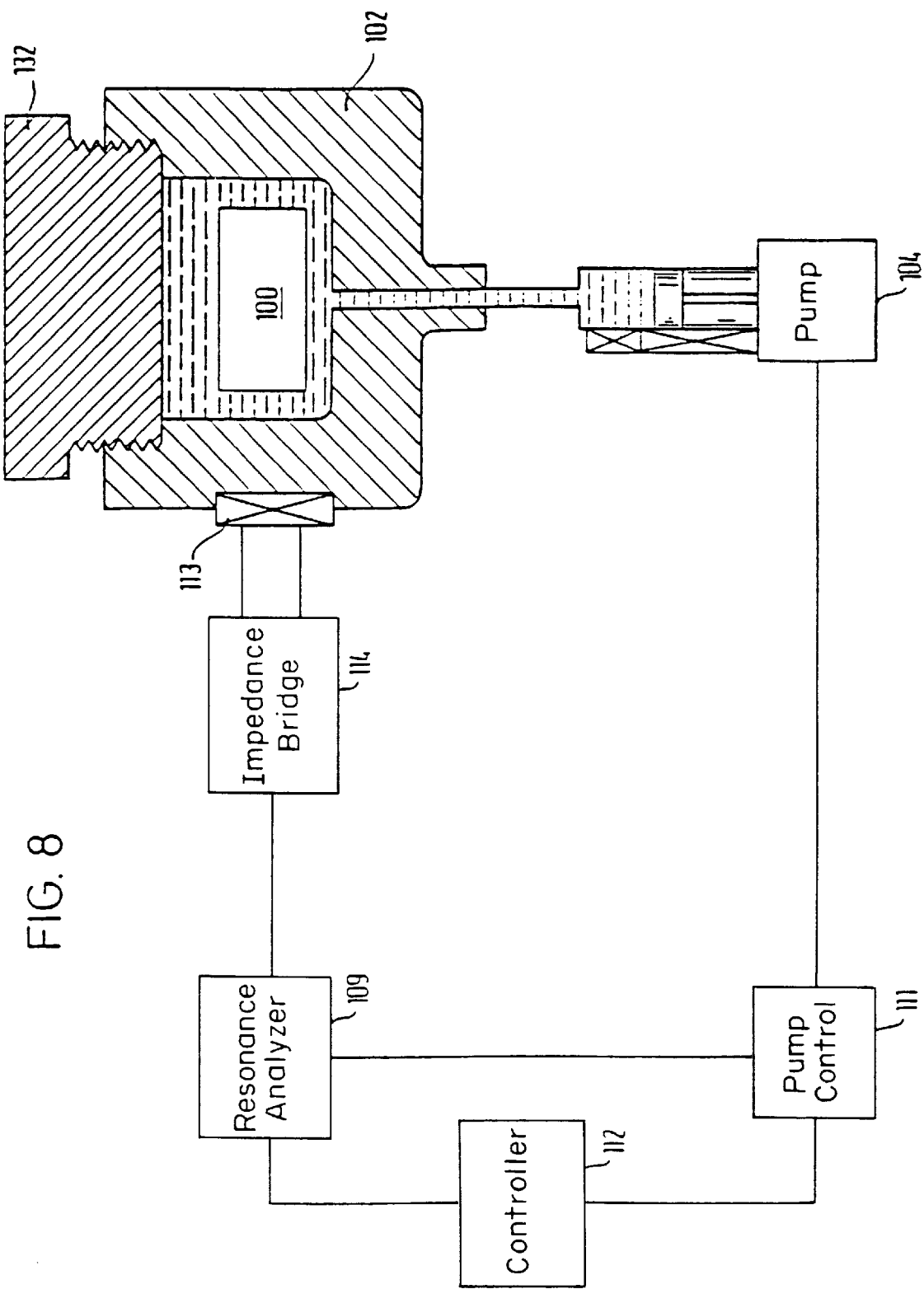

A further improvement of the invention is illustrated in FIG. 8. In this case, an acoustic transducer 113 is connected to vessel 102 to sense the acoustic resonance frequencies thereof under various conditions. Variations of the shape or geometry of the vessel caused by different inner pressures result in variations of the vessel's resonance and the relation between shape variations and resonance variations, once being known, allow tight control of mechanical effects which might deteriorate the results of the desired measurements.

It will also be possible, by making use of those relations, to achieve a desired pressure within the vessel by introducing the output signal of transducer 113 into a control loop for pump 104. The output impedance of transducer 113 depends on the mechanical vibrations to which it is subjected. By coupling transducer 113 to an impedance bridge 114, impedance variations caused by variations of the resonance of vessel 102 are being detected. Bridge 114 generates a signal representative of the actual impedance of transducer 113, and such signal is being applied to circuit 109 converting it into signals adapted for being coupled to memory and control circuit 112 and to pump control circuit 111. Pump 104 then will be controlled until the pressure within vessel 102 has the desired value. In this way, it will be possible to achieve a desired pressure within vessel 102 more quickly and exactly than when relying on resonator 108 in FIG. 7.

The embodiment of FIG. 8 advantageously allows monitoring of vessel aging by observing the changes of the resonance of the vessel when not being under pressure: In the course of the life time of the vessel its mechanical resonance frequency will vary and the amount of such variations between successive control measurements will give an indication of the aging process from which it can be determinated whether or not the vessel can be used any longer for high precision measurements.

Figure 9:
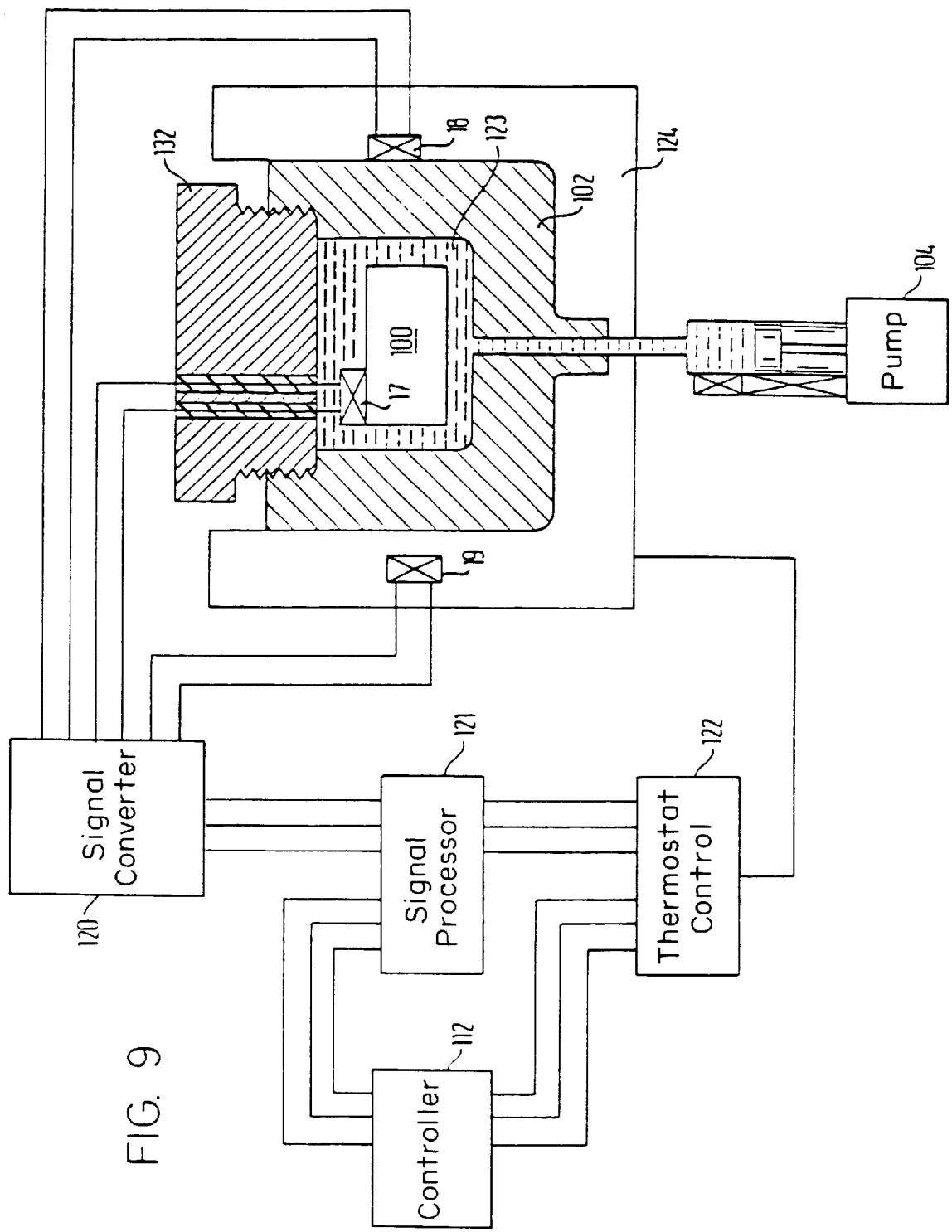

FIG. 9 shows an embodiment of the invention which allows a very tight temperature control by using a plurality of temperature sensors 17, 18 and 19 of high resolution and precision distributed at various locations of cell 100, pressure vessel 102 and thermostats 124. The output signals of such sensors are supplied to unit 120 transforming those signals into appropriate electrical signals for being used as input signals to processing circuit 121 including highly stable and accurate differential amplifiers. Deviations from reference signals supplied from memory and control circuit 112 are being used for generating control signals applied to control circuit 122 generating control signals for being applied to appropriate heating or cooling means associated to thermostat 124. By using a plurality of temperature sensors at different locations it will be possible to early recognize temperature variations so as to initiate a compensating control resulting in more precisely maintaining desired temperature conditions.

A preferred frequency range for the ultrasonic waves is above about $10^5$ Hz up to about several $10^7$ Hz.

EXAMPLES FOR THE EVALUATION OF DENSITIES

4-Channel resonator cell:

Lithium niobate transducers.
$r_0=2.5$ mm, $d=7.0$ mm, $f_0=10.0$ MHz

Measurements on reference cell filled with water:
$t=25.0$ [°(°C)]
$p=997$ [kg/m$^3$]
$c=1497$ [m/s]; V. A. DelGrosso and C. W. Mader, J. Acoust. Soc. Amer. 52 (1972) 1442–1446.
$(\alpha_w f^2)=22\times10^{-15}$ [s$^2$/m]; T. Funck und F. Eggers, Fortschritte der Akustik—DAGA'85 (1985) 651–654.

First step, calculation of $f_{lim}$ for the reference cell:
$f_{lim}=[c/r_0^2(\alpha_w/f^2)]^{1/3}=[1497/(2.5\times10^{-3})^2\times22\times10^{-15}]^{1/3}=22.16$[MHz]

Second step, measurement at $f_n=nf_\pi$ calculation of $\epsilon_{abs+geo}$:
$f_n=25.110$ [MHz]
$\Delta f_n=\Delta f_{abs+geo}=6776$[Hz]
$\epsilon_{abs+geo}=10.747\times10^{-12}$[s]

Third step, measurement of $\Delta f_n$ at $f_n=28{,}934$ [MHz]:
$\Delta f_n=11125$ [Hz]; $f_0=9.999$ [MHz]
$\Delta f_{abs+geo}=10.747\times10^{-12}$[s]$\times(28.934\times10^6$[Hz]$)^2=8997$ [Hz]
$\Delta f_{refl}=\Delta f_n-\Delta f_{abs+geo}=11125-8997=2128$[Hz]
$-\ln(\cos\theta)=\Delta f_{refl}\times\pi\times7.0\times10^{-3}$[m]$/1497$[m/s]$=0.031261$
$-\ln(\cos\theta)=0.031261\rightarrow z/tg(\pi f_n/f_0)=0.1249$
$tg(\pi f_n/f_0)=tg(\pi\times28.934/9.999)=-0.34698$
$z=0.1249\times0.34699=0.04334$
$Z_0=p\times c/z=997\times1497/0.04334=34.437\times10^6$[kg/m$^2$s]

Measurement on sample cell 1, filled with 0.100 m NaCl $\Delta f_n$ at $f_n 29.057$ [Mz]:
$f_n=29.057$[MHz]; $\Delta f_n=11897$[Hz]; $f_0=9.999$ [MHz]
$\Delta f_{abs+geo}=10.747\times10^{-12}$[s]$\times(29.057\times10^6$[Hz]$)^2=9074$ [Hz]
$\Delta f_{refl}=\Delta f_n-\Delta f_{abs+geo}=11897-9074=2823$[Hz]
$-\ln(\cos\theta)=\Delta f_{refl}\times\pi\times7.0\times10^{-3}$[m]$/1503.4$[m/s]$=0.04129$
$-\ln(\cos\theta)=0.04129\rightarrow z\times tg(\pi f_n/f_0)=0.1436$
$tg(\pi f_n/f_0)=tg(\pi\times29.057/9.999)=-0.30424$
$z=0.1436\times0.30424=0.043700$
$p=Z_0\times z/c=34.437\times10^6\times0.043700/1503.4=1001$[kg/m$^3$]
p measured by densitometer 1001[kg/m$^3$].

Measurement on sample cell 2, filled with 0.050 m NaCl $\Delta f_n$ at $f_n=28.996$ [MHz]:
$f_n=28.996$[MHz]; $\Delta f_n=11481$[Hz]; $f_0=9.999$ [MHz]
$\Delta f_{abs+geo}=10.747\times10^{-12}$[s]$\times(28.996\times10^6$[Hz]$)^2=9036$ [Hz]
$\Delta f_{refl}=\Delta f_n-\Delta f_{abs+geo}11481-9036=2445$[Hz]
$-\ln(\cos\theta)=\Delta f_{refl}\times\pi\times7.0\times10^{-3}$[m]$/1500.2$[m/s]$=0.03584$
$-\ln(\cos\theta)=0.03584\rightarrow z\times tg(\pi f_n/f_0)=0.13378$
$tg(\pi f_n/f_0)=tg(\pi\times28.996/9.999)=-0.32530$
$z=0.13378\times0.32530=0.04352$
$p=Z_0\times z/c=34.437\times10^6\times0.043520/1500.2=999$[kg/m$^3$]
p measured by densitomeer 999 [kg/m$^3$].

Appendix

Look-up table for conversion of $\ln(\cos\theta)$ into $(J=z/tg(f_n/f_0))$

| J | $-\ln(\cos\theta)$ |
|---|---|
| 0 | 0 |
| 0.05 | 0.0050 |
| 0.10 | 0.0200 |
| 0.15 | 0.0460 |
| 0.20 | 0.0800 |
| 0.25 | 0.1252 |
| 0.30 | 0.1805 |
| 0.35 | 0.2462 |
| 0.40 | 0.3228 |
| 0.45 | 0.4107 |
| 0.50 | 0.5108 |
| 0.55 | 0.6245 |
| 0.60 | 0.7538 |
| 0.65 | 0.9015 |
| 0.70 | 1.0721 |
| 0.75 | 1.2730 |
| 0.80 | 1.5163 |
| 0.85 | 1.8257 |
| 0.90 | 2.2541 |
| 0.95 | 2.9711 |

-continued

| J | -ln(cosθ) |
|---|---|
| 0.96 | 3.1991 |
| 0.97 | 3.4917 |
| 0.98 | 3.9021 |
| 0.99 | 4.6002 |
| 0.999 | 6.9073 |
| 0 | 0 |
| 0,10 | 0,0200 |
| | 0.0042 |
| 0,11 | 0,0242 |
| | 0.0046 |
| 0.12 | 0.0288 |
| | 0.0050 |
| 0.13 | 0.0338 |
| | 0.0054 |
| 0.14 | 0.0392 |
| | 0.0058 |
| 0.15 | 0.0450 |
| | 0.0062 |
| 0.16 | 0.0512 |
| | 0.0066 |
| 0.17 | 0.0578 |
| | 0.0070 |
| 0.18 | 0.0648 |
| | 0.0074 |
| 0.19 | 0.0722 |
| | 0.0078 |
| 0.20 | 0.0800 |

We claim:

1. A method of generating fluid parameters for one or more liquid samples in which the acoustical resonance behavior of said liquid samples is investigated by applying ultrasonic waves of varying frequency to said liquid samples in an ultrasonic resonator containing a plurality of resonator cells, said method comprising the steps of:

filling one of said resonator cells with a reference fluid to form a reference liquid filled resonator cell;

determining at least one resonant frequency of said ultrasonic waves in said reference liquid filled resonator cell, wherein said resonant frequency lies in a predetermined frequency range above a frequency limit associated with said reference liquid filled resonator cell, and wherein diffraction effects of said ultrasonic waves in said reference liquid filled resonator cell can be neglected;

filling at least another one of said resonator cells with one of said liquid samples to form at least one sample liquid filled resonator cell;

applying said ultrasonic waves at said resonant frequency to said sample liquid filled resonator cell;

varying the phase of said ultrasonic waves to determine a first frequency value at which said ultrasonic waves in said sample liquid filled resonator cell have a first amplitude equal to a maximum amplitude level, and second and third frequency values at which said ultrasonic waves have second and third amplitudes at a predetermined level lower than said maximum amplitude level.

2. A system for measuring fluid parameters of one or more liquids by an ultrasonic method, said system comprising:

a voltage controlled oscillator for generating a voltage controlled oscillator output signal, said voltage controlled oscillator comprising a control input terminal and an output terminal, said;

an ultrasonic resonator comprising one or more resonator cells, each of said resonator cells comprising:

an electro-acoustical transmitting transducer comprising an input terminal, said transmitting transducer input terminal being connected to said voltage controlled oscillator output terminal and driven by said voltage controlled oscillator output signal;

an electro-acoustical receiving transducer for generating a receiving transducer output signal, said receiving transducer comprising an output terminal, and a sample cavity arranged between said transmitting and receiving transducers;

a phase locked loop circuit comprising one of said resonator cells;

means for generating an ultrasonic frequency signal of variable frequency and applying said ultrasonic frequency signal to said transmitting transducer;

means connected to said receiving transducer output terminal for generating a signal responsive to said receiving transducer output signal;

means for providing a phase control voltage for controlling and varying the phase of said ultrasonic frequency signal; and means for providing a frequency control voltage for selecting a frequency for said ultrasonic frequency signal applied to said transmitting transducer according to a particular resonance peak of said resonator cells.

3. The system of claim 2, wherein said phased locked loop comprises:

a phase comparator for comparing the phase difference between said voltage controlled oscillator output signal and said signal responsive to said receiving transducer output signal; said phase comparator comprising:

a first phase comparator input terminal connected to said receiving transducer;

a second phase comparator input terminal connected to said voltage controlled oscillator output terminal; and a phase comparator output terminal for providing a phase comparator output signal;

a feedback path connecting said phase comparator output terminal to said control input terminal of said voltage controlled oscillator to form said phase locked loop; and means for disabling said phase locked loop.

4. The system of claim 3, wherein said means for disabling said phased locked loop comprises means for interrupting said phased locked loop provided in said feedback path.

5. The system of claim 3, wherein said feedback path comprises an integrator comprising:

an integrator input terminal connected to said phase comparator output terminal;

an integrator output terminal connected to said control input terminal of said voltage controlled oscillator for providing an integrator output signal;

means for resetting said integrator comprising an integrator control terminal, wherein said integrator provides a fixed voltage at said integrator output terminal when in a reset state.

6. The system of claim 3, further comprising:

means for providing a first variable voltage; and means for combining said first variable voltage with an output signal of said phase comparator output signal.

7. The system of claim 6, further comprising:

means for providing a second variable voltage; and means for combining said second variable voltage with said integrator output signal.

8. The system of claim 2, further comprising:

means connected to said voltage controlled oscillator output terminal for measuring the frequency of said voltage controlled oscillator output signal;

a gate pulse generator for providing a gate pulse, said gate pulse defining a counting interval;

means for counting oscillations provided by said voltage controlled oscillator during said counting interval, said counting means comprising means for calculating a frequency associated with said counting interval and said oscillations provided by said voltage controlled oscillator.

9. The system of claim 8, wherein said gate pulse generator comprises:

a stabilized oscillator for generating a preset number of oscillations, said stabilized oscillator comprising an output terminal;

a presettable counter for counting said preset number of oscillations from said stabilized oscillator, and for generating an output pulse while counting and defining said counting interval, said presettable counter comprising a start input terminal;

means for synchronizing an external start signal connected to said stabilized oscillator output terminal, said synchronizing means comprising:

an output connected to said start input terminal of said presettable counter, wherein said presettable counter counts only during at a defined time when said stabilized oscillator generates said preset number of oscillations;

an enabling input terminal for application of an enabling signal.

10. The system of claim 2, further comprising means for measuring the amplitude of said receiving transducer output signal, said amplitude measuring means being connected to said receiving transducer output terminal.

11. The system of claim 10, wherein said amplitude measuring means comprises:

amplitude limiting means for generating a sign signal, said amplitude limiting means comprising:
an input terminal connected to said receiving transducer output terminal, and
an output terminal for providing said sign signal;

a multiplier for multiplying said sign signal with said receiving transducer output signal to obtain a unidirectional multiplier output signal, said multiplier comprising:
a first multiplier input terminal connected to said receiving transducer output terminal; and
a second multiplier input terminal connected to said output terminal for said amplitude limiting means; and means for processing said unidirectional multiplier output signal, said processing means generating a signal representing the amplitude of said receiving transducer output signal, said processing means comprising an analog-to-digital converter, said analog-to-digital converter comprising an input terminal and an output terminal.

12. The system according to claim 11, further comprising an averaging circuit for selectively connecting said analog-to-digital converter input terminal to said integrator output terminal, and for receiving said integrator output signal representing the phase of said ultrasonic frequency signal.

13. The system according to claim 2, further comprising:

a plurality of said resonator cells adapted to be selectively connected into said feedback path between said voltage controlled oscillator and said phase comparator;

means for switching said resonator cells in and out of said feedback path between said voltage controlled oscillator and said phase comparator, said switching means comprising:
a first multiplexer comprising an input terminal connected to said voltage controlled oscillator output terminal, and a plurality of output terminals respectfully connected to said transmitting transducers of said resonator cells; and
a second multiplexer comprising a same plurality of input terminals respectfully connected to said receiving transducers of said resonator cells; and an output terminal connected to said phase comparator.

14. The system of claim 13, wherein said output terminal of said second multiplexer is connected to said phase comparator through said amplitude limiting means.

15. The system of claim 13, wherein one of said resonator cells is a reference cell defining a standard condition.

16. The system of claim 2, further comprising:

a pressurized fluid contained within at least one of said resonator cells; and a pressure-tight vessel for housing said at least one of said resonator cells containing said pressurized fluid.

17. The system of claim 16, wherein a solid-state resonator is housed within said pressure-tight vessel.

18. The system of claim 16, further comprising an additional transducer mechanically connected to said pressure-tight vessel for measuring acoustic resonance variations thereof during different mechanical stress conditions, said additional transducer exhibiting an impedance that depends on mechanical vibrations to which said transducer is subject.

19. The system of claim 18, further comprising:

an impedance bridge for generating a signal representative of said acoustic resonance of said pressure-tight vessel, said impedance bridge being connected to said additional transducer; and a memory and control circuit for controlling said system, wherein said signal representative of said acoustic resonance of said pressure-tight vessel is provided to said memory and control circuit.

\* \* \* \* \*

UNITED STATES PATENT AND TRADEMARK OFFICE
CERTIFICATE OF CORRECTION

PATENT NO. : 5,804,698

DATED : September 8, 1998

INVENTOR(S) : Belonenko et al.

It is certified that error appears in the above-identified patent and that said Letters Patent is hereby corrected as shown below:

Column 1, line 24, "$10^6$" should read -- $10^{-6}$ --;

Column 11, line 59, "p" should read -- $\rho$ --;

Column 12, line 16, "p" should read -- $\rho$ --;

Column 12, line 17, "$\Delta f_n$" should be deleted;

Column 12, line 18, "at $f_n 29.057$ [Mz];" should read -- $\Delta f_n$ at $f_n = 29.057$ [MHz]: -- ;

Column 12, line 29, "p" should read -- $\rho$ -- ;

Column 12, line 30, "p" should read -- $\rho$ -- ;

Column 12, line 31, "$\Delta f_n$" should be deleted;

UNITED STATES PATENT AND TRADEMARK OFFICE
CERTIFICATE OF CORRECTION

PATENT NO. : 5,804,698

DATED : September 8, 1998

INVENTOR(S) : Belonenko et al.

It is certified that error appears in the above-identified patent and that said Letters Patent is hereby corrected as shown below:

Column 12, line 32, "at $f_n$=28.996 [MHz]:" should read -- $\Delta f_n$ at $f_n$ = 28.996 [MHz]: -- ;

Column 12, line 42, "p" should read -- $\rho$ -- ;

Column 12, line 43, "p" should read -- $\rho$ -- .

Signed and Sealed this

Twelfth Day of December, 2000

Attest:

Q. TODD DICKINSON

*Attesting Officer*     *Director of Patents and Trademarks*